United States Patent [19]

Lentz et al.

[11] Patent Number: 4,668,224
[45] Date of Patent: May 26, 1987

[54] OXIDIZED CELLULOSE AS A MEDICAL LUBRICANT

[75] Inventors: David J. Lentz, Salt Lake City; Mohammad A. Khan, Sandy, both of Utah

[73] Assignee: Warner-Lambert Company, Morris Plains, N.J.

[21] Appl. No.: 544,665

[22] Filed: Oct. 24, 1983

[51] Int. Cl.³ ............................................. A41D 19/04
[52] U.S. Cl. .................................. 604/265; 604/292; 2/161 R; 2/168
[58] Field of Search ............... 2/161 R, 168; 604/292, 604/293, 265

[56] References Cited

U.S. PATENT DOCUMENTS 2,507,244 5/1950 Correll ..................................... 2/168
3,861,396 1/1975 Vaillancourt et al. .............. 604/265

Primary Examiner—C. Fred Rosenbaum
Assistant Examiner—Harrie R. Samaras
Attorney, Agent, or Firm—Louis S. Gillow

[57] ABSTRACT

The use of oxidized cellulose as a medical lubricant is disclosed wherein oxidized cellulose is employed as a mold release agent or a donning powder in the manufacture of surgical gloves as well as in other applications; medical devices and, particularly, a surgical glove, are provided having finely divided oxidized cellulose powder on the surface in a lubricity imparting coverage.

19 Claims, No Drawings

OXIDIZED CELLULOSE AS A MEDICAL LUBRICANT

BACKGROUND OF THE INVENTION

The present invention relates to medical lubricants such as gloving powders and mold release agents and, more particularly, to the use of oxidized cellulose in these capacities.

Post-operative complications such as adhesions, peritonitis, and granuloma formation have been attributed to the use of non-absorbable lubricants on surgical gloves and other surgical elements. Talc powders, for years, were used as dusting powders for surgical gloves until it was found that they caused severe foreign body reactions in patients. As a result, talc powders were replaced by bioabsorbable starch powders of the type disclosed in U.S. Pat. No. 2,626,257 to Caldwell et al (1953). Even starch particles, however, have been implicated in the production of granulomatus lesions. Some researchers attribute starch granuloma to the presence of talc and other non-absorbable inorganics in the starch, whereas other researchers believe that in some cases the starches are so highly cross-linked that they cannot be sufficiently absorbed by the body tissue. As a result, there is a need for a medical lubricant which is more readily absorbable and free from or accompanied by less severe foreign body reactions.

Efforts directed to providing an absorbable, granuloma-free medical lubricant have provided the following materials:

U.S. Pat. No. 2,864,743 to Kestler et al (1958): a modified starch particle obtained by condensing a magnesium or aluminum salt with epichlorohydrin etherified starch.

U.S. Pat. No. 2,938,901 to Kerr et al (1960): starch esterified in its unswollen granule state by reaction with a water soluble metaphosphate salt.

U.S. Pat. No. 3,122,482 to Smith (1964): calcium salts of phosphated or sulfated starches.

U.S. Pat. No. 3,133,866 to Richardson (1964): inorganic powders such as talc in admixture with an acid salt of the polybasic phosphoric acid.

U.S. Pat. No. 3,728,739 to Semp (1973): finely divided polyglycolic acid.

U.S. Pat. No. 4,053,3769 to Fox et al (1977): etherified starch treated with an acid or alkaline medium and heated until is exhibits a predetermined reducing power.

U.S. Pat. No. 4,064,564 to Casey (1977): enzymatically degradable forms of poly(N-acetyl-D-glucosamine).

U.S. Pat. No. 4,143,423 to Sternlieb (1979): sodium and potassium salts such as sodium or potassium carbonate, bicarbonate, acetate, acetate trihydrate, and citrate dihydrate.

U.S. Pat. No. 4,152,783 to Choski (1979): water soluble inocuous powders such as sodium bicarbonate.

U.S. Pat. No. 4,310,928 to Joung (1982): lipids and lipophilic compounds such as fatty acids, fatty acid esters and lipophilic particles and an associated surfactant added to a coagulant bath as a mold release agent.

Oxidized cellulosse has been found useful in various medical/surgical applications in the past, but its use as a donning powder or medical lubricant has not been suggested. For example, V. Frantz, "New Absorbable Hemostatic Agents", *Bull N.Y. Acad. Med.*, 22: 102,1946 showed that is could be used as a carrier for thrombin and had useful hemostatic properties of its own. Cellulose partially oxidized by periodate has also been studied in the immobilization of trypsin (*Biotech. and Bioeng*, 16: 997–1003, 1974) and chyrotrypsin (Singh et al, "Potential Biosoluble Carriers: Biocompatibility and Biodegradability of Oxidized Cellulose", *Biomat., Med. Dev., Art. Orig.*, 7(4), 495–512 (1979)), and it has been tested for implantation in body tissues to prevent adhesions.

SUMMARY OF THE INVENTION

In accordance with the present invention it has been found that finely divided oxidized cellulose powder (also known as acid cellulose) is useful as a medical lubricant on the surfaces of such devices as surgical gloves, condoms, catheters, drains, tubes and the like. More particularly, it has been found that oxidized cellulose powder is a useful glove donning powder and mold release agent.

Medical lubricants and, particularly, the medical lubricants used in conjunction with surgical gloves as donning powders or mold release agents must be biocompatible and capable of sterilization by such commonly employed techniques as autoclaving, gamma irradiation, and ethylene oxide sterilization. Oxidized cellulose satisfies these requirements. It is insoluble in water, but, when neutralized with an alkaline solution, it becomes soluble and sufficiently bioabsorbable that it can be completely absorbed by body tissue without producing granulomous lesions. Body fluids are believed to quickly neutralize oxidized cellulose particles and convert it into a salt which is water soluble. The body's defense mechanism then gradually digests the material, probably by a hydrolytic route. Thus, oxidized cellulose powder can be used as a mold release agent or a donning powder in the manufacture of surgical gloves. It imparts the desired degree of lubricity and it appears to be completely absorbable with minimal tissue reaction.

Thus, one embodiment of the present invention provides a surgical glove having on the surface thereof a lubricity imparting amount of a finely divided oxidized cellulose powder.

Another embodiment of the present invention provides a process for lubricating the surfaces of surgical devices such as catheters, condoms, drains and the like which comprises applying to the surfaces of said devices a lubricity imparting amount of oxidized cellulose.

Still another embodiment of the present invention provides a process for forming surgical gloves in which the improvement resides in applying oxidized cellulose to the surface of the glove mold as a mold release agent.

DETAILED DESCRIPTION OF THE INVENTION

The oxidized cellulose preferred for use in the present invention is prepared by reacting cellulose with oxides of nitrogen (e.g., $NO_2$ or $N_2O_4$) in a known manner. Nitrogen oxides preferentially react with the primary hydroxyl groups in the cellulose to generate a product which has been shown to be a copolymer of anhydroglucuronic acid. One example of a powdered oxidized cellulose suitable for use in the present invention is commercially available from Tennessee Eastman Company, Kings Port, Tenn. For a detailed discussion of the synthesis of oxidized cellulose, reference can be made to U.S. Pat. No. 3,364,200 to Ashton et al (1968) and U.S. Pat. No. 2,232,990 to Kenyon (1941).

Another material suitable for the present invention is oxidized cellulose prepared by periodate oxidation of cellulose (see *Methods in Carbohydrate Chemistry*, page 165–168, Academic Press, New York and London (1963)).

The degree of oxidation of the cellulose will vary depending upon the time of the treatment and the relative proportion of the oxidizing agent to cellulose used in the manufacturing process. The oxidized cellulose used in the present invention preferably has a carboxyl content of about 8–15% by weight. Carboxyl content can be determined by adding 50 ml of carbon dioxide-free water and 30 ml of 0.5N calcium acetate solution to a 0.5 gram sample of oxidized cellulose at 25° C. After standing 2 hours, 30 ml portions of the liquid are titrated with 0.1N sodium hydroxide. Carboxyl contents are calculated by the equation:

$$\frac{\text{ml of 0.1 N NaOH} \times 0.0045 \times 100 \times 8}{\text{Sample weight} \times 3} = \text{wt. \% COOH}$$

The theoretical maximum carboxyl content obtained by oxidation with nitrogen oxide has been determined to be about 25.6%, but is is usually not practical to oxidize cellulose beyond about 22%. The range of 8–18% by weight is preferred in the present invention because it provides a optimum balance of water insolubility and bioabsorbability. These celluloses are further characterized in that they provide a pH of about 1.0 to 3.5 in a 1% aqueous solution.

Oxidized cellulose is used as a medical lubricant in accordance with the present invention in the form of a finely divided powder. The preferred particle size can vary with the particular application in which the lubricant is used, but the powder typically ranges from about 4 to 60 microns in particle size.

When used as a mold release agent, finely divided oxidized cellulose powder can be sprayed upon a glove form in a known manner to provide a uniform coating sufficient to prevent a subsequently applied glove-forming latex or resin composition from adhering to the mold. Alternatively, finely divided oxidized cellulose powder is dispersed into a coagulant system with divalent or trivalent cationic inorganic salts soluble in water. The coagulant system may also contain small amounts of dispersing agents such as commercially available and pharmaceutically acceptable surfactants. The coagulant is applied by dipping the glove form therein, followed by drying at low heat (about 98° to 127° C.) for about 5 to 10 minutes. Thereafter, a film-forming latex or resin composition is applied to the glove form, and the film is dried and cured in a conventional manner to provide the glove. After removing the glove from the form, because oxidized cellulose is bioabsorbable, it is not necessary to thoroughly wash the gloves as it is when talc is used as the mold release agent. In fact, in accordance with the present invention, gloves manufactured using oxidized cellulose as the mold release agent can subsequently be dusted with oxidized cellulose powder to facilitate donning.

Oxidized cellulose can be applied to surgical gloves as a donning powder (regardless of whether it has been used as a mold release agent in manufacturing the glove) by tumbling the gloves in a bed of the powder such that the powder adequately covers the internal surfaces of the glove or by immersing the glove in a fluidized bed of powder. To remove the powder from the outside of the gloves and remove the excess powder from the inside of the gloves after tumbling, the gloves are usually tumble polished. Other medical devices such as drains, condoms, tubes and the like can be powder-coated with oxidized cellulose in accordance with the present invention in a known manner.

The dusted gloves and surgical devices can be sterilized by conventional practices. The preferred methods are by gamma irradiation and ethylene oxide treatment. Some instability to autoclaving has, however, been noted and therefore this practice should be avoided.

The biocompatibility of oxidized cellulose as a medical lubricant has been comfirmed by histophathologic studies wherein polypropylene and Mersilene suture segments were dusted with oxidized cellulose powder having a particle size of about 4 to 60 microns and a carboxyl content of about 11 to 13% by weight. The dusted suture segments were implanted in the abdominal intramuscular region of Sprague Dawley rats (180–200 grams) using standard aseptic operating room techniques. In the first weeks following implantation a moderate inflammatory response with a predominance of histiocytic cells and some eosinophila has been noted, but no giant cells have been observed. By the fourth week, the inflammatory response has subsided and by the sixth to eighth week, a well-informed capsule is generally observed around the wound sutures.

Having described the invention in detail and by reference to specific embodiments thereof, it will be apparent that numerous modifications are possible without departing from the spirit and scope of the invention defined by the following claims.

What is claimed is:

1. A surgical glove having on at least one surface thereof a lubricity imparting amount of finely divided oxidized cellulose powder.

2. The surgical glove of claim 1 wherein said oxidized cellulose has a particle size of about 4 to 60 microns.

3. The surgical glove of claim 2 wherein said oxidized cellulose has a carboxyl content of about 8–18% by weight.

4. The surgical glove of claim 3 wherein said oxidized cellulose provides a pH of about 1.0 to 3.5 in a 1% aqueous solution.

5. The surgical glove of claim 4 wherein said oxidized cellulose is obtained by reacting cellulose with a nitrogen oxide.

6. The surgical glove of claim 4 wherein said oxidized cellulose is obtained by reacting cellulose with a periodate.

7. A medical device such as condom, catheter, drain, tube, or the like having on the surface thereof a lubricity imparting amount of finely divided oxidized cellulose.

8. The medical device of claim 7 wherein said oxidized cellulose has a particle size of about 4 to 60 microns.

9. The medical device of claim 8 wherein said oxidized cellulose has a carboxyl content of approximately 8–18% by weight.

10. The medical device of claim 9 wherein said oxidized cellulose provides a pH of about 1.0 to 3.5 in a 1% aqueous solution.

11. The medical device of claim 10 wherein said oxidized cellulose is the product of reacting cellulose with an oxide of nitrogen.

12. The medical device of claim 10 wherein said oxidized cellulose is the product of reacting cellulose with a periodate.

13. A process for lubricating the surfaces of surgical devices such as catheters, condoms, tubes, drains, and the like, which comprises applying to a surface of said device a lubricity imparting amount of oxidized cellulose.

14. The process of claim 13 wherein said oxidized cellulose has a particle size of about 4 to 60 microns.

15. The process of claim 14 wherein said oxidized cellulose has a carboxyl content of approximately 8-18% by weight.

16. The process of claim 15 wherein said oxidized cellulose provides a pH of about 1.0 to 3.5 in a 1% aqueous solution.

17. The process of claim 16 wherein said oxidized cellulose is prepared by reacting cellulose with an oxide of nitrogen.

18. The process of claim 16 wherein said oxidized cellulose is prepared by reacting cellulose with a periodate.

19. A cellulose lubricated surgical glove formed by the process of any of claims 13 to 24.

* * * * *